United States Patent [19]

Hogg

[11] 4,438,390
[45] Mar. 20, 1984

[54] TANDEM SENSING ZONES FOR IMPROVED SIGNAL-TO-NOISE RATIO IN PARTICLE ANALYZER

[75] Inventor: Walter R. Hogg, Miami, Fla.

[73] Assignee: Coulter Electronics, Inc., Hialeah, Fla.

[21] Appl. No.: 246,755

[22] Filed: Mar. 23, 1981

[51] Int. Cl.³ ............................................. G01N 27/00
[52] U.S. Cl. .................................... 324/71.1; 377/11; 377/12
[58] Field of Search ................. 324/71 CP, 71.1, 71.4; 235/92 PC; 377/10–12; 364/555

[56] References Cited

U.S. PATENT DOCUMENTS 3,924,180 12/1975 Salzman et al. ................ 324/71 CP
4,161,690 7/1979 Feier ............................... 324/71 CP

*Primary Examiner*—Michael J. Tokar
*Assistant Examiner*—Kevin D. O'Shea
*Attorney, Agent, or Firm*—Gerald R. Hibnick

[57] ABSTRACT

A tandem arrangement of sensing zones is established by alternately arranged electrodes and dielectric plates, each sensing zone has a particle sensing aperture, through which microscopic particles in an electrolyte suspension pass and electric current flows. The apertures are aligned. This tandem sensing zone arrangement improves the signal-to-noise ratio of a particle analyzing apparatus in which it is employed.

18 Claims, 8 Drawing Figures

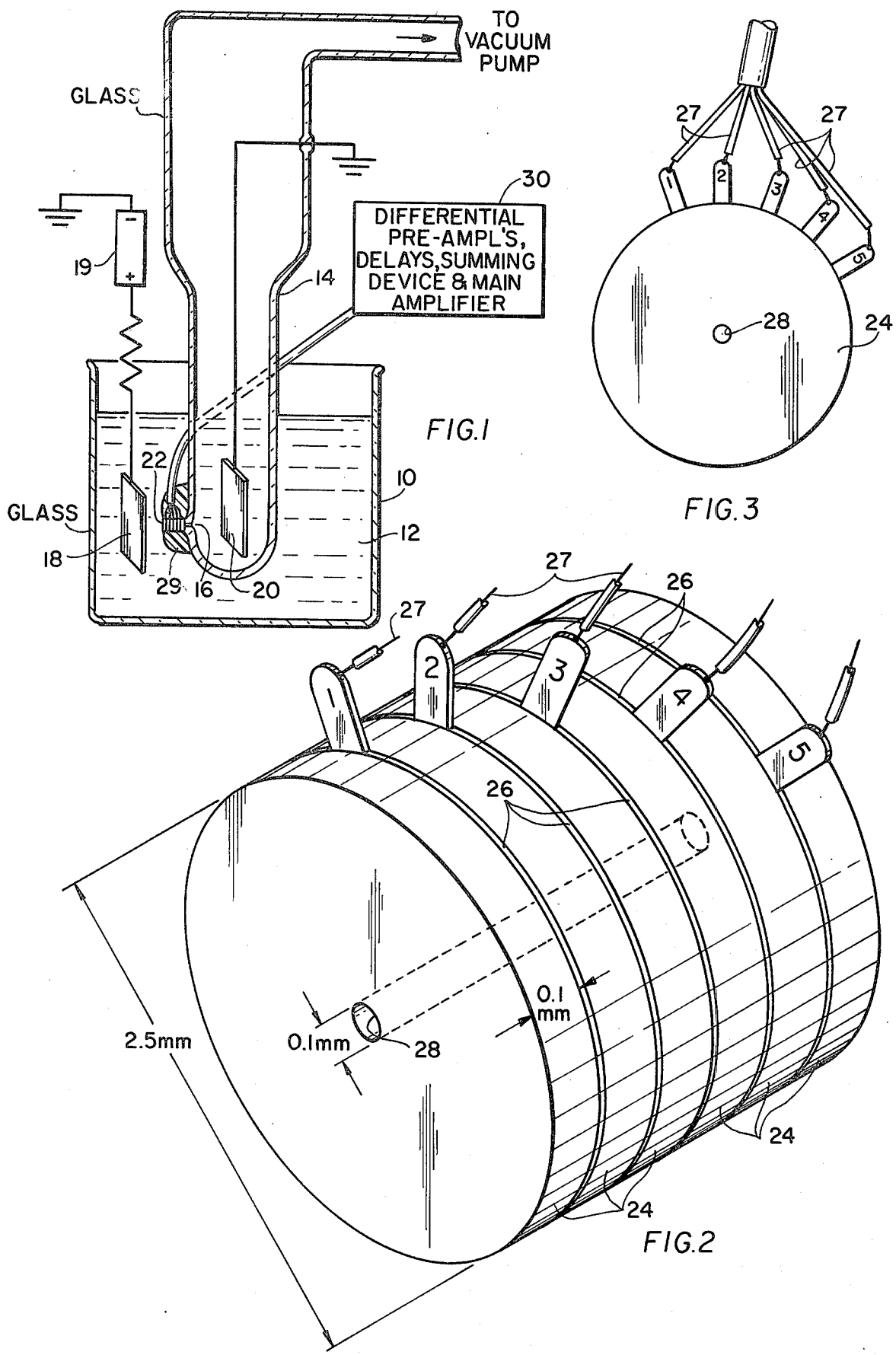

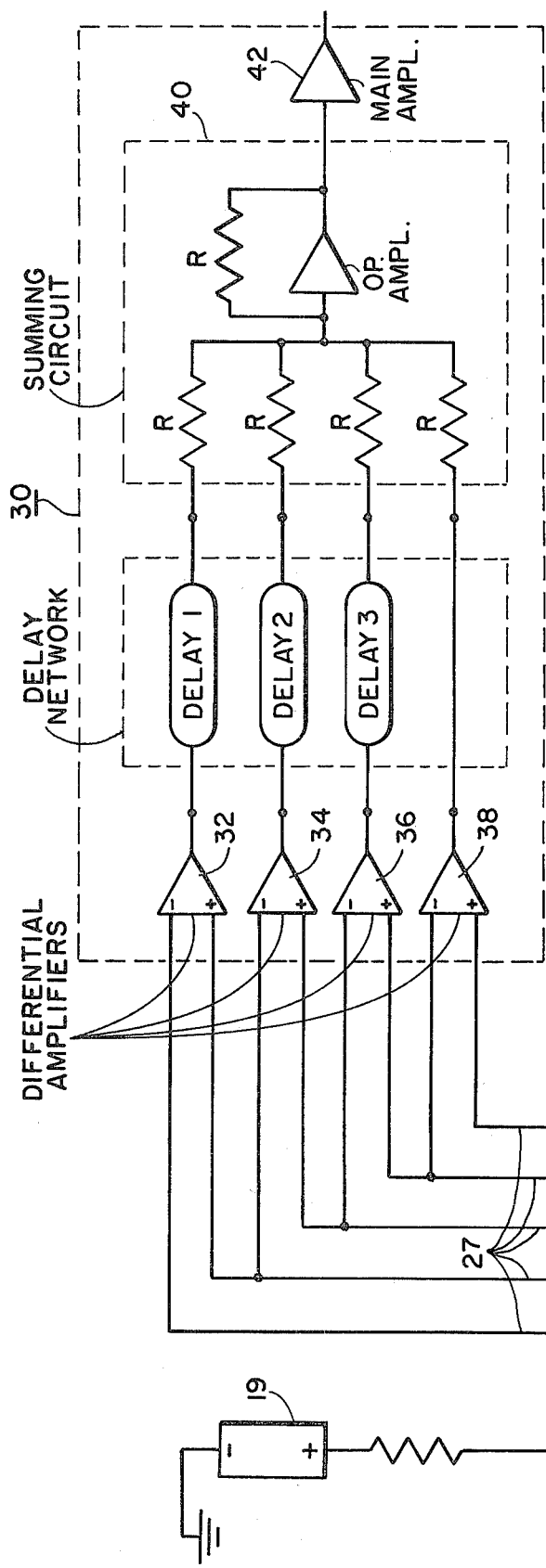
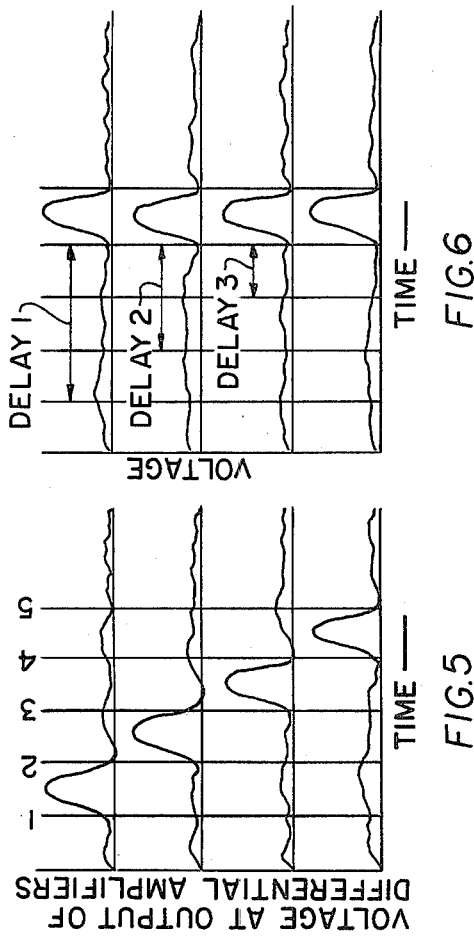
FIG.6
FIG.5
FIG.4

TANDEM SENSING ZONES FOR IMPROVED SIGNAL-TO-NOISE RATIO IN PARTICLE ANALYZER

The present invention relates to particle counting and analyzing apparatus, and particularly to a method of and apparatus for improving the Signal-to-Noise ratio of such apparatus operating on the Coulter principle.

BACKGROUND OF THE INVENTION

The Coulter principle or mode of operation is disclosed in Coulter U.S. Pat. No. 2,656,508. This patent discloses an apparatus for counting and classifying particles suspended in an electrically conducting liquid. Two containers or vessels are in fluid communication with one another through a microscopically small measuring aperture. The passage of a microscopic particle suspended in the conducting liquid of one container through the aperture whose dimensions approximate those of the particles causes a change in the resistance of the electric path through the liquid effectively contained in the aperture, assuming that the material of the particle in the liquid has an electrical conductivity different from that of the liquid. Suitable electrodes in the two containers are immersed in the conducting liquid on both sides of the aperture and are connected to an electrical current source and measuring circuit. The change in electrical resistance results in a change in electrical current flowing through the liquid as the particle moves through the aperture. The magnitude of the change in electrical resistance (or voltage) is a measure of the size of the particle moving through the aperture.

Variations of the apparatus disclosed in the Coulter U.S. Pat. No. 2,656,508 appear in U.S. Pat. Nos. 3,710,933; 3,259,842; 3,793,587; 3,924,180; 3,944,917; 4,019,134 and East German Pat. No. 66,038.

U.S. Pat. No. 3,793,587 discloses two spaced-apart measuring apertures of different dimensions arranged in tandem, whereby a particle volume measurement may be obtained at one measuring aperture and a particle cross-section measurement may be obtained at the other measuring aperture. Two apertures of different geometry are essential to the operation of the system disclosed in this patent. One aperture must be long enough to contain in the region of uniform field strength the entire volumes of the particles moving through it, while the other aperture has a shorter length to evaluate essentially particle cross-sections.

U.S. Pat. Nos. 3,924,180 and 4,019,134 both disclose apparatus for electrically analyzing biological cells wherein an orifice having two potential sensing electrodes is immersed in the container of the electrically conducting liquid in which the cells or particles to be analyzed are suspended. The orifice is positioned adjacent and aligned with the aperture in the other container, whereby the entrance to the orifice communicates with the particle suspension and the exit of the orifice communicates with the aforesaid aperture for evacuating the cell or particle containing liquid through the orifice and aperture.

East German Pat. No. 66,038 discloses a lamination of dielectric bodies and alternately appearing metal electrodes constituting one-half of an assembly through which particles are designed to pass. The other half of the assembly is a cover in the form of a single integral block of insulation. A conduit passes through the assembly between the two halves. In one embodiment described in the patent pin-like electrodes protrude or jut into the conduit. No suggestion appears in the patent for the need of a smooth hydrodynamic flow path for the particles passing through the conduit.

The foregoing patents provide the prior art background for an understanding of the operation of the Coulter system of which the present invention is an outgrowth. The descriptions in these patents are to be considered as though bodily incorporated herein.

A problem encountered in particle counting and analyzing apparatus operating on the Coulter principle of the type described, for example, in U.S. Pat. Nos. 3,924,180 and 4,019,134, is the noise due to the Johnson effect (thermal noise due to random motion of charges in the conductive liquid or electrolyte). This random noise places a limit on the smallest size of the particle which can be counted and analyzed by the apparatus.

U.S. Pat. No. 4,019,134 discloses a multiple sensing electrode flow cell, but does not have multiple particle sensing zones and is used to make the signals independent of the liquid conductivity.

SUMMARY OF THE INVENTION

An object of the present invention is to further improve the signal-to-noise ratio in a particle counter and analyzer system which operates on the principle of Wallace Coulter.

Another object is to enable the Coulter Counter ® to count and analyze particles of smaller size than could be the case where the noise signals due to the Johnson effect is significant. "Coulter Counter" is a registered trademark of Coulter Electronics, Inc.

A feature of the invention is the improved miniature laminated structure of a plurality of alternately arranged sensing electrodes and dielectric discs which provide a plurality of sensing zones. A measuring aperture or orifice of uniform diameter is drilled through the entire thickness of the laminated structure to enable the particles in liquid suspension to flow smoothly through all sensing zones.

Another feature of the invention is the circuitry which algebraically adds the desired signals from the plurality of sensing zones of the laminated structure while adding the noise signals as the square root of the sum of the squares, thereby providing a significant increase in the useful output in signal-to-noise (S/N) ratio.

A preferred embodiment of the invention utilizes a container, for example, a beaker holding an electrically conducting liquid, such as a saline solution, in which particles or cells to be counted and analyzed are suspended. Immersed in the vessel is a laminated structure constituting a plurality of sensing zones arranged in tandem and through the entire length of which there is a smooth unobstructed bore of uniform geometry made up of a plurality of measuring apertures, one for each sensing zone. The laminated structure comprises alternately arranged electrodes and dielectric discs. The entrance of the bore communicates with the particle-containing conducting liquid in the container and the exit of the bore communicates with a device via a hole in the device which is appreciably larger than said aperture for evacuating the particle-containing liquid through the bore of uniform geometry. The apertures are aligned in a straight line with the aforesaid hole. Individual differential amplifiers in one embodiment of the invention are connected to the different sensing zones. Delay circuits in the outputs of the differential amplifiers are so sized as to cause the delayed outputs to occur simultaneously. These delayed outputs are additively combined in a summing circuit, whereby the desired useful signal pulses are added algebraically while the undesired noise signals add as a square root of the sum of the squares.

BRIEF DESCRIPTION OF THE DRAWINGS

FIG. 1 schematically illustrates an apparatus embodying the principles of the invention. Parts of this figure of the drawing are shown in section;

FIG. 2 diagrammatically illustrates in grossly exaggerated form the laminated structure forming the plurality of tandemly arranged sensing zones of the apparatus of the invention shown in FIG. 1;

FIG. 3 is a front view of FIG. 2 looking into the entrance of the orifice or opening which passes completely through the laminated structure;

FIG. 4 schematically illustrates one embodiment of the system of the invention showing how the electrical circuitry is connected to the tandemly arranged sensing zones of the apparatus of FIG. 1 for achieving a better signal-to-noise ratio;

FIG. 5 graphically illustrates the time-voltage relationship of the useful and noise signal waveforms appearing in the outputs of the differential amplifiers;

FIG. 6 graphically illustrates the time-voltage relationship of the useful and noise signal waveforms of FIG. 5 after the outputs from the differential amplifiers have passed through delay networks of different selected values, and as supplied to the operational amplifier.

Figure 7:
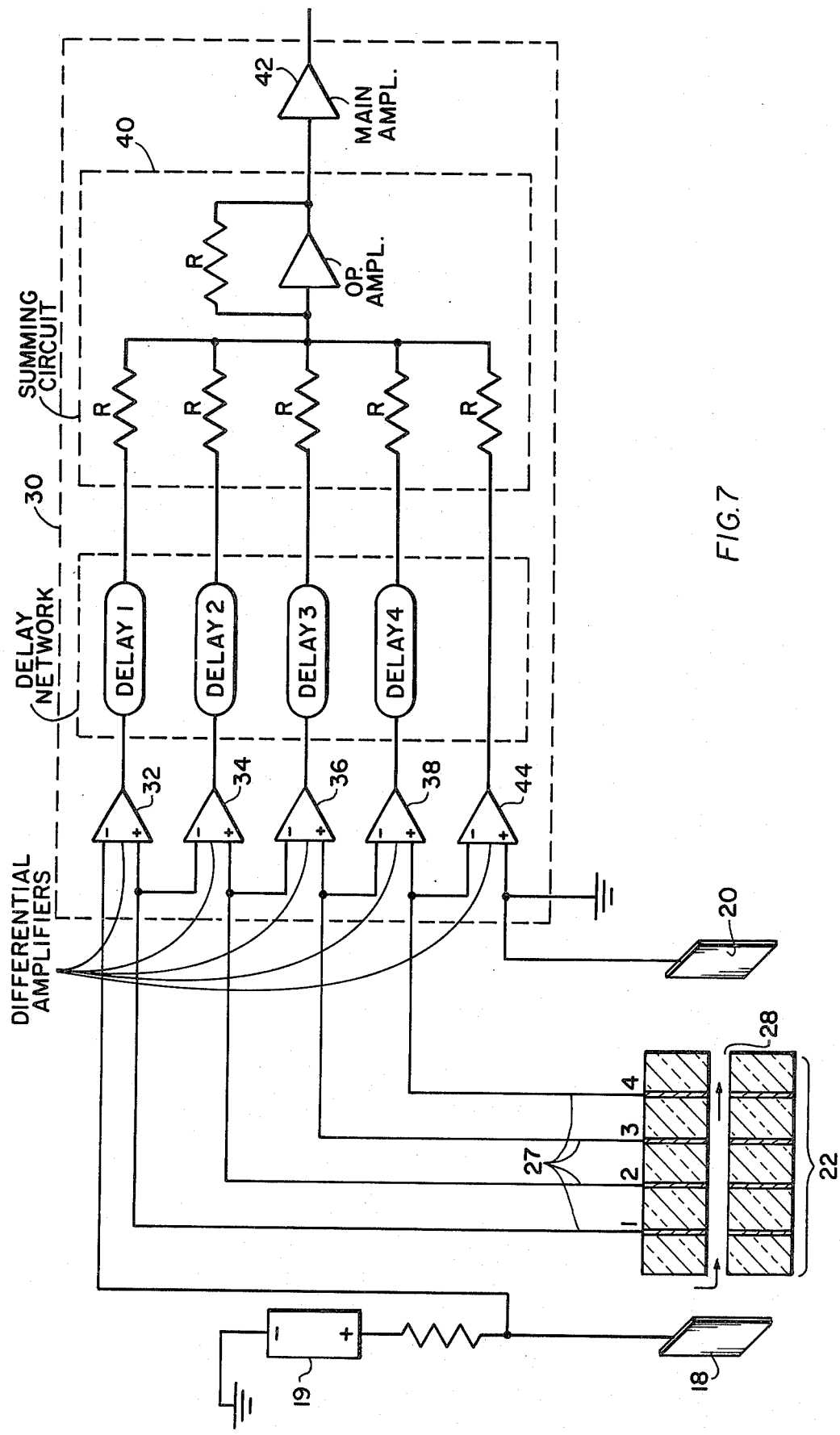
FIGS. 7 and 8 illustrate other embodiments of the system of the invention.

The sizes of the laminated structure forming the multi-sensing zones of FIGS. 1 and 2 have been exaggerated in the interest of clarity. Typical useful sizes are given numerically in FIG. 2.

Throughout the figures of the drawings the same parts are designated by same reference numerals.

DETAILED DESCRIPTION OF PREFERRED EMBODIMENT

That portion of the particle analyzing or studying apparatus of FIG. 1 which comprises the glass container 10 containing a suspension of particles to be analyzed in an electrically conducting liquid 12, the glass container 14 having a hole 16, the power electrodes 18 and 20 in the two containers on opposite sides of the hole, and the coupling of the container 14 to a vacuum pump for aiding in moving the particle suspension from container 10 through hole 16 into container 14 is well known in the art for studying the physical properties of the particles in the liquid. The liquid may be a saline solution such as that known by the trade-name ISO-TON II, a phosphate buffered solution of sodium chloride manufactured by Coulter Diagnostics, Inc., a division of Coulter Electronics, Inc. of Hialeah, Fla. Examples of such known particle analyzing apparatus and associated electrical circuitry are disclosed in the aforesaid U.S. patents.

What is novel in the practice of the present invention is the multi-sensing zone feature 22 comprising preferably a laminated structure of alternately arranged dielectric discs and electrodes forming a plurality of sensing zones arranged in tandem and through all zones of which passes a bore 28 of uniform geometry unobstructed to the smooth flow of particles therethrough, and the electrical circuitry 30 for achieving an improved signal-to-noise ratio, whereby useful pulse signals representative of the particles to be analyzed add algebraically while the noise signals add as the square root of the sum of the squares. This electrical circuitry includes individual differential amplifiers for the different sensing zones and delay networks for causing the useful pulse signal outputs from the differential amplifiers to occur simultaneously. A summing circuit which includes an operational amplifier is coupled to the output ends of the delay networks.

The tandemly arranged multi-zone laminated structure 22 is located between the power electrodes 18 and 20 and has its smooth bore 28 aligned with the hole 16 in the container 14. Laminated structure 22 comprises a plurality of equal dimensioned discs 24 of dielectric material alternating with equal dimensioned disc-shaped metallic electrodes 26. The dielectric material 24 should be hard, smooth, durable, impermeable to moisture and highly polished to enhance the hydrodynamic flow of the liquid. One such suitable dielectric is synthetically grown sapphire. The metal electrodes may be in the form of a film adjacent to the dielectric, and is prefereably platinum which resists corrosion. Other metals such as silver and copper may be used. These electrodes may partially rather than completely encircle the bore 28 of uniform geometry which passes completely through the laminated structure for enabling particles in suspension in container 10 to smoothly pass completely through the structure and through the hole 16 into the glass container 14. The electrodes 26 have terminals 1 to 5 for enabling electrical connections to the electrical circuitry 30. These terminals are offset from one another, as shown in FIGS. 2 and 3 in view of the miniature size of the component parts of the laminated structure 22 to enable ease in soldering the wire connections 27 to the terminals.

All electrical connections in the apparatus which are adapted to be immersed in the conducting liquid have electrical insulation sheaths to prevent short-circuiting and leakage problems which would cause incorrect measurements. Due to the small size of the assembly 22, it is expedient to embed the entire exterior, including the electrical connections in a drop 29 of some suitable insulation material such as epoxy, in such manner however, as not to obstruct the entrance and exit of the bore 28 through which the liquid passes.

The operation of the system of the invention will now be given with particular reference to FIGS. 4, 5 and 6. The containers and the liquids therein shown in FIG. 1 have not been illustrated in FIG. 4. Only the essential elements necessary for an understanding of the electrical operation of the system have been shown in FIG. 4. Thus, containers 10 and 14, the hole 16 and the conducting liquid of FIG. 1 required for a complete particle sensing apparatus have been omitted from FIG. 4 though it should be understood that they are present in the apparatus in the manner generally illustrated in FIG. 1.

The particle sensing zones in the laminated structure 22 may be defined as the distance between terminals 1 and 2, the distance between terminals 2 and 3, the distance between terminals 3 and 4, and the distance between terminals 4 and 5. These distances are equal.

Terminals 1 and 2 are electrically connected to high impedance differential amplifier 32. Terminals 2 and 3 are electrically connected to high impedance differential amplifier 34. Terminals 3 and 4 are electrically connected to high impedance differential amplifier 36. Terminals 4 and 5 are electrically connected to high impedance differential amplifier 38.

An electric current supply 19 preferably as described in U.S. Pat. No. 4,019,134 delivers current which flows through the bore 28 and hole 16 between electrodes 18 and 20.

The particle-containing saline liquid solution passes through bore 28 of the laminated structure, through the respective apertures of the sensing zones in tandem, as indicated by the arrows, into container 14 drawn by a vacuum effected by a vacuum pump coupled as shown in FIG. 1 to the interior of container 14. As a particle passes through each sensing zone, for example between the platinum electrodes having terminals 1 and 2, it varies the potential across these electrodes because the conductivity of the particle is different from that of the saline solution itself. This conductivity difference causes a change in resistance across the aperture in the sensing zone being traversed by the particle. The change in resistance is proportional to the volume of the particle. The aperture resistance change multiplied by the aperture current from supply 19 gives a potential change or potential difference which appears at the input of the high impedance differential amplifier which, in turn, provides an amplified difference pulse output. Thus, the sensing zones being traversed in tandem by the particle pass their respective potential changes to their respective differential amplifiers in sequence.

The outputs of the differential amplifiers 32 to 38 are pulses which are displaced in time as illustrated by the waveforms of FIG. 5. The numerals 1 to 5 at the top of FIG. 5 are indicative of the sensing zones defined by the spacings between the terminals 1 to 5 of the sensing electrodes 26. The small amplitude waveform variations along the base lines of each pulse represent the electrical noise.

The outputs of differential amplifiers 32, 34 and 36 pass through different selectively valued delay networks (delay 1, delay 2 and delay 3) so sized that the pulses from the output ends of the delay networks occur at the same time as the pulse output from differential amplifier 38, as illustrated by the waveforms of FIG. 6. The delay networks may be a series of inductances shunted by capacitances or charge-coupled semi-conductor devices as well known in the art.

The output pulses from the delays and from the last differential amplifier pass through equal valued resistors R in a summing circuit 40 where they are combined to cause the particle pulses to add algebraically while the noise adds as the square root of the sum of the squares as will appear from the following mathematical reasoning:

Let $S_1$ = the signal voltage between the first two sensing electrodes $S_2$ = the signal voltage between the 2nd and 3rd electrodes $S_n$ = the signal voltage between the nth and the $(n+1)^{th}$ electrodes $N_1$ = the noise voltage between 1st and 2nd electrodes $N_2$ = the noise voltage between 2nd and 3rd electrodes $N_n$ = the noise voltage between the nth and the $(n+1)^{th}$ electrodes If the signals are all equal and delayed such that they occur simultaneiously and are added together, we have the resultant signal $$S = S_1 + S_2 + \ldots S_n = nS_1 = nS_2 \text{ etc.}$$

Since noise is completely random in amplitude and phase, one can only add powers rather than voltages; it follows that the noise signals do not add algebraically but as the square root of the sum of their squares.

Resultant noise voltage $$N = \sqrt{N_1^2 + N_2^2 + N_3^2 + \ldots N_n^2}$$

The resistances between electrodes are typically equal, and hence their root-mean-square noise voltages are equal. Thus $$N = \sqrt{n N_n^2} = \sqrt{n} \sqrt{N_n^2} = \sqrt{n} \, N_n$$

The signal-to-noise ratio of any one aperture is $(S_n/N_n)$. The signal-to-noise ratio at the output of the summing circuit is $$\frac{nS_n}{\sqrt{n} \, N_n} = \sqrt{n} \, \frac{S_n}{N_n}$$

Hence the improvement achieved by the invention is the ratio of the two S/N ratios, or $$\frac{\frac{\sqrt{N} \, S_n}{N_n}}{\frac{S_n}{N_n}} = \sqrt{N}$$

This can be tabulated thus:

| no. of sensing zones = n | improvement in S/N ratio | improvement expressed in d b |
|---|---|---|
| 2 | 1.414 | 3.01 |
| 3 | 1.732 | 4.77 |
| 4 | 2 | 6.02 |
| 5 | 2.24 | 6.99 |
| 6 | 2.45 | 7.78 |

The summing circuit includes an operational amplifier having a feedback circuit which includes a resistor R. The output from the differential amplifier feeds a main amplifier 42 which, in turn, is coupled to suitable particle-size threshold circuits and data processing circuits.

The system of the invention provides an appreciable decibel increase in the signal-to-noise ratio, as a result of which the size of the particles or cells being measured can be smaller than would ordinarily be measureable by counters and analyzers not equipped with the present invention. As an example, a 3 db increase in signal-to-noise ratio enables a particle counter designed to measure particles or cells of one cubic micron to measure cells or particles of 0.7 cubic micron size when equipped with the present invention.

FIG. 7 is a modification of the system of the invention of FIG. 4 mainly in the use of power electrode 18 both as a power electrode and as a sensing electrode. It should be noted that power electrode 18 is connected to a differential amplifier 32, and that power electrode 20 is connected to differential amplifier 44. The terminals 1 to 4 of electrodes 26 of assembly 22 are connected to the differential amplifiers somewhat differently from those in the system of FIG. 4 in order to achieve the desired results. Except for these changes the system functions generally in the manner hereinabove described for the system of FIG. 4.

Figure 8:
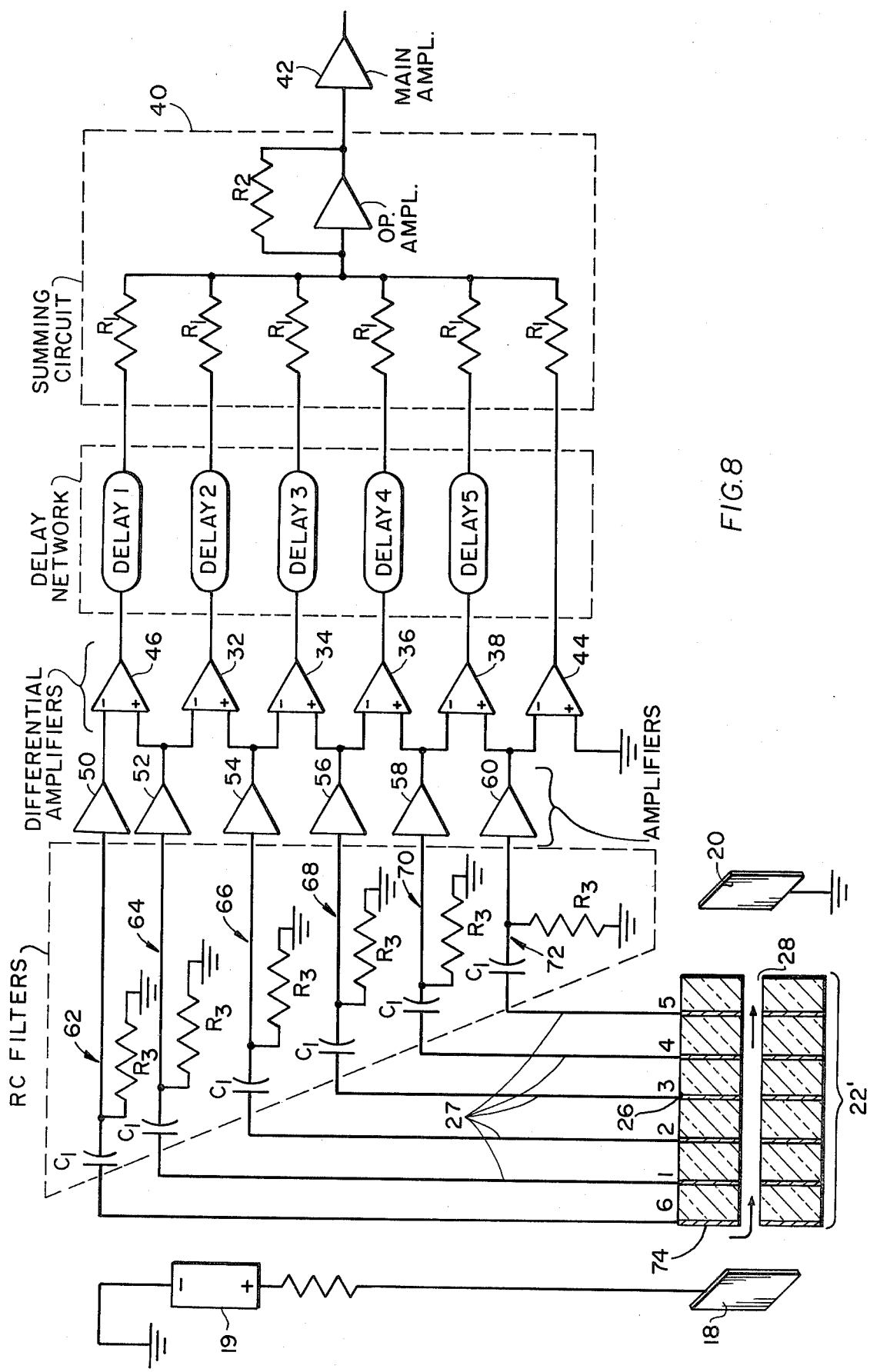

FIG. 8 is another embodiment of the invention. The system of FIG. 8 is generally the same as the system of FIG. 7, except that there is provided a single-ended input amplifier 50, 52, 54, 56, 58 or 60 between each of a plurality of RC filters 62, 64, 66, 70 or 72 and its associated differential amplifier 46, 32, 34, 36, 38 or 44. The RC filters 62, 64, 66, 68, 70 and 72 are coupled to electrode terminals 6, 1, 2, 3, 4 and 5, respectively. Again, this embodiment makes use of both of the end sensing zones which are nearest the entrance and exit of the bore aperture 28. To illustrate that the use of the end sensing zones can be accomplished in numerous ways, the sensing zone near the entrance of the bore aperture 28 utilizes a sensing electrode 74, without using the power electrode 18.

As can be seen from FIG. 7, the power electrodes 18 and 20 can be used to form the end sensing zones, with the power electrodes also serving as sensing electrodes. Alternatively, a separate set of sensing electrodes can be used in addition to the power electrodes, in a manner illustrated in U.S. Pat. No. 4,019,134 to Hogg. These sensing electrodes can be either suspended in the containers 10 and 14 in a similar manner as the power electrodes 18 and 20, or they can be attached to the outer walls of the laminated structure or flow cell 22, such as illustrated by the electrode 74 in FIG. 8. Also, as illustrated in FIG. 4, the end sensing zones do not need to be utilized. It will be obvious to those skilled in the art that there are numerous ways in which the various electrodes can be combined to create the consecutive sensing fields.

The embodiments of the drawings have illustrated the flow cell 22 as having four or six separate and individual particle sensing zones. However, it should be understood that in the broadest scope of the invention, only two separate sensing zones are necessary for obtaining a better signal-to-noise ratio. The greatest incremental improvement in the signal-to-noise ratio is brought about by the combination of the first two sensing zones, with each additional sensing zone adding a smaller incremental improvement in the ratio. The simplest structure correlating two sensing zones is the use of only two dielectric discs or plates 24 with one electrode 26 sandwiched therebetween. In such a case, a pair of power electrodes or sensing electrodes would be positioned in the containers 10 and 14 for completing the two sensing fields. Additional dielectric plates 24 and electrodes 26 can be added as desired, with each additional dielectric plate creating another sensing zone, which in turn provides a better signal-to-noise ratio.

Referring to the different embodiments of the drawings, the differential amplifiers 32 through 46 are high impedance amplifiers that consume a negligible current so that voltage pulses for the passing particles are detected. However, it will be obvious to those skilled in the art that, although less desirable, low impedance amplifiers could be used so as to detect current pulses representing the passing of the particles. In such a case, the current should be minimized so as to lessen polarization effects. Any such polarization effects can be minimized by using fluid electrodes in place of the illustrated metal electrodes 26. In other words, there would be channels in place of the electrodes 26 filled with fluid that would be in fluid communication with a spaced-apart fluid vessel containing the metal electrode. Except for large particle analyzers, such fluid electrodes are undesirable due to the difficulty in fabricating such small channels. However, the scope of the invention as described by the appended claims is intended to cover electrodes sandwiched between adjacent dielectric plates 24 which are either metal or fluid electrodes. In either case, each dielectric plate 24 defines a separate particle sensing zone.

The order of the signal manipulations of subtracting the signals using the differential amplifiers, delaying the signals with delay networks, amplifying and filtering the signals can be accomplished in any sequence desired. For instance, the voltages are subtracted by the differential amplifiers first in the embodiments of FIGS. 4 and 7, but in FIG. 8, the signals are filtered and amplified before being subtracted. Although not specifically illustrated, there are numerous other combinations of pulse manipulations that will be obvious to those skilled in the art, such as delaying the pulses prior to undertaking the other pulse manipulations.

The preferred design of the embodiments has the bore aperture 28 with a uniform cross-sectional configuration. However, it is within the scope of the invention to vary the diameter and, although achieving inferior results, still accomplish the objectives of the invention. For instance, the bore aperture 28 could be provided with a decreasing diameter, resulting in the particles generating stronger voltage pulses with each successive sensing zone. This could be approximately compensated for by varying the resister values of summing circuit so that the pulses from each sensing zone would be given approximately the same weight. However, it is highly desirable to keep the cross-sectional dimensions uniform throughout the bore aperture 28 so that each sensing zone will generate a voltage pulse of similar magnitude and width.

Variations in the number of tandemly arranged sensing zones in the laminated structure can be made without departing from the spirit and scope of the invention as defined in the appended claims. The more sensing zones comprising pairs of spaced electrodes in the laminated structure the greater will be the signal-to-noise ratio. The first and last dielectric discs shown in FIG. 2 are not essential to the practice of the invention. The component elements of the laminated structure may, in one form, be laminated by a high quality adhesive or by epoxy. The platinum electrodes 26 are thin films which are deposited onto the sapphire dielectric discs 24 and the electrodes 26 have been bonded together as an integral assembly, the bore 28 is then preferably drilled through the entire laminated structure in one straight line so that all openings in the tandem zones line up and are of identical geometry. The result is a laminated assembly having a smooth bore devoid of discontinuities or obstructions, thereby providing a highly desirable hydrodynamic flow path through the bore for the electrolyte and the particles immersed therein.

Although the preferred embodiment of the invention provides a plurality of apertures which register with each other need not be in a straight line but may deviate from said straight line.

The term "dielectric" used herein is deemed to include any electrically insulative material; the preferred material having high thermally conductive properties, a hardness to resist abrasion and mechanical damage, being chemically resistant to corrosion, and impermeable to water. Examples of such materials are sapphire and glass.

I claim:

1. A particle analyzing apparatus for detecting properties of particles, said particle analyzing apparatus including a first vessel for holding a conductive liquid having a suspension of said particles, a second vessel for holding a conductive liquid, a flow cell having an aperture formed therethrough to provide a constricted liquid passageway between said first vessel and said second vessel, means for moving a quantity of the conductive liquid from said first vessel through said aperture and into said second vessel, means for providing current through said aperture, the improvement comprising:

an arrangement, including said flow cell, of alternately arranged sensing electrodes and dielectric plates wherein each dielectric plate can define a separate particle sensing zone, there being at least three of said sensing electrodes and at least two of said dielectric plates with one of said sensing electrodes being sandwiched between the two said dielectric plates, said flow cell being formed by said dielectric plates and at least said sensing electrode sandwiched therebetween with said aperture passing therethrough;

means electrically coupled to a pair of sequentially located said sensing electrodes on opposed sides of each of at least two said dielectric plates to separately detect electrical pulses produced by particles passing through each of the said dielectric plates;

means for delaying at least all but the last of said electrical pulses for each particle so that said electrical pulses occur simultaneously; and means for summing said simultaneous electrical pulses; whereby an improved signal to noise ratio is achieved.

2. The particle analyzing apparatus according to claim 1, wherein said means electrically coupled to sequentially located said sensing electrodes for detecting said electrical pulses includes a differential amplifier for each said pair of sequentially located sensing electrodes, said differential amplifier having one input connected to one electrode of said pair of sequentially located sensing electrodes and another input connected to the other electrode of said pair of sequentially located sensing electrodes.

3. The particle analyzing apparatus according to claim 2, wherein said differential amplifier comprises a high impedance amplifier, whereby voltage pulses are detected.

4. The particle analyzing apparatus according to claim 3, wherein said means for delaying said voltage pulses includes a delay circuit coupled to the output of at least each said differential amplifier except the last.

5. The particle analyzing apparatus according to claim 4, wherein said means for delaying said voltage pulses includes a delay circuit coupled to the output of each said differential amplifier.

6. The particle analyzing apparatus according to claim 1, wherein two of said at least three sensing electrodes are in spaced apart relationship to said flow cell, one being positioned in said first vessel and the other positioned in said second vessel.

7. The particle analyzing apparatus according to claim 1, wherein said at least two dielectric plates comprise at least three dielectric plates and one of said sensing electrodes is positioned in one of said vessels in spaced apart relationship to said flow cell.

8. The particle analyzing apparatus according to claim 1, wherein said at least two dielectric plates comprise at least four dielectric plates, wherein all of said sensing electrodes are separately sandwiched between adjacent said dielectric plates.

9. The particle analyzing apparatus according to claim 1, wherein said at least two dielectric plates comprise a plurality of dielectric plates and said at least three sensing electrodes comprising a plurality of sensing electrodes, there being at least two of said sensing electrodes being individually sandwiched between said dielectric plates.

10. The particle analyzing apparatus according to claim 1, wherein said means for providing a current through said aperture comprising a pair of power electrodes coupled to an energizing source, one of said power electrodes being positioned in each of said vessels.

11. The particle analyzing apparatus according to claim 10, wherein said power electrodes also serve as sensing electrodes.

12. The particle analyzing apparatus according to claim 10, wherein at least one of said vessels has one of said sensing electrodes positioned therein, in addition to said power electrode, whereby said power electrode is not used as a sensing electrode.

13. The particle analyzing apparatus according to claim 1, wherein the cross-sectional configuration of said apreture is kept constant.

14. The particle analyzing apparatus according to claim 1, wherein said flow cell comprises a lamination of said sensing electrodes and said dielectric plates.

15. Apparatus analyzing particles suspended in an electrically conducting liquid, comprising, in combination, a structure of alternately arranged electrodes and dielectric plates constituting sensing zones arranged in tandem, said structure having measuring apertures aligned and spaced from one another, there being an aperture for each zone, means for advancing said suspension through said aperture, whereby the particles pass successively through said sensing zones, means for passing an electric current through each of said apertures, means electrically coupled to pairs of sequentially located said electrodes to individually detect the electrical pulses produced by particles passing through at least each of two said dielectric plates; means for delaying at least all but the last of said electrical pulses for each particle so that said pulses occur simultaneously, and means for summing said simultaneous electrical pulses.

16. The particle analyzing apparatus according to claim 15, wherein said means electrically coupled to sequentially located said electrodes for detecting said electrical pulses includes a differential amplifier for each said pair of sequentially located electrodes, said differential amplifier having one input connected to one electrode of said pair of sequentially located electrodes and another input connected to the other electrode of said pair of sequentially located electrodes.

17. The particle analyzing apparatus according to claim 16, wherein said means for delaying said electrical pulses includes a delay circuit coupled to the output of at least each said differential amplifier except the last.

18. A method of improving the signal-to-noise ratio in apparatus for studying particles suspended in a conducting liquid, said apparatus including a plurality of sensing zones having aligned apertures arranged in tandem and through which the suspended particles are adapted to pass in sequence, which comprises advancing said suspension through said aligned apertures, passing an electrical current through said aligned apertures to electrically produce a signal in each sensing zone as a particle passes through said zone, delaying the signals so that they occur simultaneously, and additively combining the delayed signals, whereby particle-produced signals are enhanced in value compared to random noise.

* * * * *